US005723328A

United States Patent [19]

Dalboege et al.

[11] Patent Number: 5,723,328
[45] Date of Patent: Mar. 3, 1998

[54] ENZYME WITH ENDOGLUCANASE ACTIVITY

[75] Inventors: Henrik Dalboege, Virum; Lene Nonboe Andersen, Birkeroed; Lene Venke Kofod, Ugerloese; Markus Sakari Kauppinen, Copenhagen; Stephan Christgau, Vedbaek, all of Denmark

[73] Assignee: Novo Nordisk A/S, Bogsvaerd, Denmark

[21] Appl. No.: 446,660

[22] PCT Filed: Dec. 23, 1993

[86] PCT No.: PCT/DK93/00444

§ 371 Date: May 26, 1995

§ 102(e) Date: May 26, 1995

[87] PCT Pub. No.: WO94/14953

PCT Pub. Date: Jul. 7, 1994

[30] Foreign Application Priority Data

Dec. 23, 1992 [DK] Denmark ................................. 1544/92

[51] Int. Cl.$^6$ .................. C12N 1/15; C12N 15/56; C12N 15/63; C12N 21/00
[52] U.S. Cl. ............... 435/209; 435/254.11; 435/254.2; 435/254.3; 435/320.1; 435/325; 536/23.2
[58] Field of Search ................ 435/320.1, 240.2, 435/254.11, 254.2, 254.3, 209, 325; 536/23.2

[56] References Cited

FOREIGN PATENT DOCUMENTS

WO 93/17101  9/1993  WIPO .
WO 93/20193  10/1993  WIPO .

OTHER PUBLICATIONS

Nishitani et al., Journal of Biochemistry, vol. 267, No. 29, pp. 21058–21064, 1992.
Hayashi et al., Plant Physiol., pp. 605–610, 1984.
McDougall et al., J. Plant Physiol., vol. 137, pp. 332–336, 1991.
Fry et al., Biochem., vol. 282, pp. 821–828, 1992.
Beldman et al., Eur. J. Biochem., vol. 146., pp. 301–308, 1985.
Sharma et al., FEMS Microbiology Letter, pp. 99–104, 1991.
Ooi et al., Nucleic Acids Research, vol. 18, No. 19, 1990.
Gilkes et al., Microbiological Reviews, vol. 55, No. 2, pp. 303–315, 1991.
Ooi et al., Curr. Genet, vol. 18, pp. 217–222, 1990.
T.M. Wood, Biotechnol. & Bioeng. Symp., No. 5, pp. 111–137, 1975.
Lee et al., Advances in Biochemical Engineering, vol. 17, pp. 101–129 (1980).
Tor–Magnus Enari, Microbial Enzymes and Biotechnology, Applied Science Publishers, pp. 183–223 (1983).
Goksøyr et al., Microbial Enzymes and Bioconversions, Academic Press, pp. 283–330 (1980).
Murao et al., Meth. Enzymol. 160:274–299, 1988.

*Primary Examiner*—Eric Grimes
*Attorney, Agent, or Firm*—Steve T. Zelson, Esq.; Valeta Gregg, Esq.

[57] ABSTRACT

An enzyme from *Aspergillus aculeatus* exhibiting endoglucanase activity, which enzyme is designated EG II or EG IV and is encoded by a DNA sequence comprising at least one of the partial sequences shown in SEQ ID NO: 17, 18, or 19. The enzyme may be produced by recombinant DNA techniques and may be used for degradation of plant cell wall material.

18 Claims, 6 Drawing Sheets

ENZYME WITH ENDOGLUCANASE ACTIVITY

CROSS-REFERENCE TO RELATED APPLICATIONS

This application is a continuation of PCT/DK93/00444 filed Dec. 23, 1993, which is incorporated herein by reference.

FIELD OF INVENTION

The present invention relates to enzymes with endoglucanase activity, a method of producing the enzymes, and an enzyme preparation containing an enzyme of the invention.

BACKGROUND OF THE INVENTION

Endoglucanases (EC no. 3.2.1.4) constitute a group of hydrolases, which catalyse endo hydrolysis of 1,4-β-D-glycosidic linkages in cellulose, cellulose derivatives (such as carboxy methyl cellulose and hydroxy ethyl cellulose) lichenin, β-1,4 bonds in mixed β-1,3 glucans such as cereal β-D-glucans or xyloglucans and other plant material containing cellulosic parts. The authorized name is endo-1,4-β-D-glucan 4-glucano hydrolase, but the abbreviated term endoglucanase is used in the present specification. Reference can be made to R. F. Gould, "Cellulases and their Application", Advances in Chemistry Series 55, American Chemical Society (1969), T. M. Wood, "Properties and Mode of Action of Cellulases", in Biotechnology and Bioengineering Symposium, no. 5, John Wiley, 111–137 (1975), Y. -H. Lee and L. T. Fan", Properties and Mode of Action of Cellulose", Advances in Biochemical engineering 17, 101–129 (1980), J. Goksøyr and J. Eriksen, "Cellulases" in A. H. Rouse, Microbial Enzymes and Bioconversions, Academic Press, 283–330 (1980), T. -M. Enveri, "Microbial Cellulases" in W. M. Fogarty, Microbial Enzymes and Biotechnology, Applied Science Publishers, 183–224 (1983).

Endoglucanases have been found to be produced by various types of organisms such as plants and microorganisms, and endoglucanases of a wide variety of specificities have been identified. For instance, xyloglucan specific endoglucanases have been identified in various plants, cf the disclosure of Fry et al. (1992), Nishitani and Tominaga (1992), Hayashi et al. (1984), McDougall and Fry (1991), and WO 93/17101. All of these enzymes have been found to have transferase activity (as defined e.g. by Fry et al., 1992 and Nishitani et al., 1992) and are not, accordingly, classified as a real endoglucanase. Hitherto, xyloglucan specific endoglucanases have not been identified in microorganisms.

Microbial endoglucanases have been described by Beldman et al., 985 (*Trichoderma viride*) and in WO 93/20193 (*Aspergillus aculeatus*), the latter reference being published only after the priority dates of the present invention. Furthermore, Sharma et al., 1991, Ooi, et al., 1990, and Gilkes et al. 1991 describe microbial endoglucanases.

Endoglucanases may advantageously be used for the degradation of cellulose components present in plant cell walls and bacterial polysaccharides. Endoglucanases having a high xyloglucan-degrading activity may be of particular use for degradations of cell wall material having a high xyloglucan content, for instance in the wine and fruit industry, for pectin-extraction and for removal of hemicelluloses from textile fibres.

The object of the invention is to provide novel endoglucanases exhibiting useful substrate specificities and a method for producing the endoglucanases in a better yield and higher purity than hitherto possible. A further object is to provide novel products, wherein the proportion of the endo-β-1,4-glucanase is either increased or decreased relative to the proportion in the original product. The endoglucanases and the novel products of the invention, whether alone or in combination with other enzymes may be used for the degradation of plant cell wall tissue.

SUMMARY OF THE INVENTION

Accordingly, in a first aspect the present invention relates to an enzyme exhibiting endoglucanase activity, which enzyme is encoded by a DNA sequence comprising at least one of the following partial sequences (a) ATTCATTTGTG GACAGTGGAC (SEQ ID No: 1)
(b) GTTGATCGCA CATTGAACCA (SEQ ID No: 2)
(c) ACCCCAGCCG ACCGATTGTC (SEQ ID No: 3)
(d) CTTCCTTACC TCACCATCAT (SEQ ID No: 4)
(e) TTAACATCTT TTCACCATGA (SEQ ID No: 5)
(f) AGCTTTCCCT TCTCTCCCTT (SEQ ID No: 6)
(g) GCCACCCTGG CTTCCGCTGC CAGCCTCC (SEQ ID No: 7)
(h) GACAGTAGCA ATCCAGCATT (SEQ ID No: 8)
(i) AGCATCAGCC GCTTTGTACA (SEQ ID No: 9)
(j) CCATGAAGTT CACCGTATTG (SEQ ID No: 10)
(k) GCACTGCTTC TCTCCCAGGT (SEQ ID No: 11)
(l) GTGGGCGGCC CCTCAGGCAA (SEQ ID No: 12)
(m) ACGCTCCTCC AATTTTCTCT (SEQ ID No: 13)
(n) GGCTTGGTAG TAATGAGTCT (SEQ ID No: 14)
(o) GGCGCAGAGT TTGGCCAGGC (SEQ ID No: 15)
(p) CAACATCCCC GGTGTTCTGGG (SEQ ID No: 16)

In the present context, the term "endoglucanase activity" is intended to indicate a capability of hydrolysing 1,4-β-D-glycosidic linkages present in any cellulosic material, such as cellulose, cellulose derivatives, lichenin, β-D-glucan, or xyloglucan. The endoglucanase activity may be determined in accordance with methods known in the art, examples of which are described in the Materials and Methods and Examples section herein. One unit of endoglucanase activity (e.g. CMCU, AVIU, XGU or BGU) is defined as the production of 1 µmol reducing sugar/min from a glucan substrate, the glucan substrate being, e.g., CMC (CMCU), acid swollen Avicell (AVIU), xyloglucan (XGU) or cereal β-glucan (BGU). The reducing sugars are determined as described in the Materials and Methods section herein. The specific activity of an endoglucanase towards a substrate is defined as units/mg of protein.

In a further aspect, the invention relates to an enzyme exhibiting endoglucanase activity, which enzyme i) is encoded by a DNA sequence comprising or included in at least one of the following partial sequences AAAGATTCATTTGTGGACAGTGGACGTTGATCGCA-
CATTGAACCAACCCCAGCCGACCGATTGTCCTT-
CCTTACCTCACCATCATTTAACATCTTTTCACCAT-
GAAGCTTTCCCTT- CTCTCCC TTGCCACCCTG-
GCTTCCGCTGCCAGCCTCCAGCGCCGCA-
CACTTCTGCGGTCAGTGGGATA
CCGCCACCGCCGGTGACTTCACCCTGTACAACG-
ACCTTTGGGG- CGAGACGGCCGGCACCGG CTC-
CCAGTGCACTGGAGTCGACTCCTA-
CAGCGGCGACACCATCGCTTGTCACAC-
CAGCAGG TCCTGGTCGGAGTAGCAG-
CAGCGTCAAGAGCTATGCCAACG (SEQ ID No: 17)
or
CAGCATCTCCATTGAGTAATCACGTTG-
GTGTTCGGTGGCCCGCCGTGTTGCGTG-
GCGGAGG CTGCCGGGAGACGGGTGGGGATGG- TGGTGGGAGAGAATGTAGGGCGCCGTGTTTCA-
GTCCC TAGGCAGGATACCGGAAAACCGTGTGG-
TAGGAGGTTTATAGGTTTCCAGGAGACGCTGTAT
AGGGGATAAATGAGATTGAATGGTGGC-
CACACTCAAACCAACCAGGTCCTGTACATACAAT
GCATATACCAATTATACCTAC-
CAAAAAAAAAAAAAAAAAAAAAAAAAAAA
(SEQ ID No: 18)

or a sequence homologous thereto encoding a polypeptide with endoglucanase activity, ii) is immunologically reactive with an antibody raised against a highly purified endoglucanase encoded by the DNA sequence defined in i) and derived from *Aspergillus aculeatus*, CBS 101.43, and/or iii) is specific for xyloglucan.

In the present context, the term "specific for xyloglucan" is intended to indicate that the enzyme exhibits a high activity on a xyloglucan substrate and only low, if any, activity on other cellulose-containing substrates such as carboxymethyl cellulose, cellulose, or other glucans.

The specificity of an endoglucanase towards xyloglucan may be defined as a relative activity determined as the release of reducing sugars at optimal conditions obtained by incubation of the enzyme with xyloglucan and the other substrate to be tested, respectively. For instance, the specificity may be defined as the xyloglucan to β-glucan activity (XGU/BGU) or xyloglucan to carboxy methyl cellulose activity (XGU/CMCU) or xyloglucan to acid swollen Avicell activity (XGU/AVIU).

In the following disclosure, the enzyme defined by properties i)–iii) above is referred to as of endoglucanase type II or (for short Endoglucanase II or EG II).

In the present context, the term "derived from" is intended not only to indicate an endoglucanase produced by strain CBS 101.43, but also an endoglucanase encoded by a DNA sequence isolated from strain CBS 101.43 and produced in a host organism transformed with said DNA sequence.

In the present context, the term "homologue" is intended to indicate a polypeptide encoded by DNA which hybridizes to the same probe as the DNA coding for an endoglucanase enzyme of the invention under certain specified conditions (such as presoaking in 5×SSC and prehybridizing for 1 h at ~40° C. in a solution of 5×SSC, 5×Denhardt's solution, and 50 µg of denatured sonicated calf thymus DNA, followed by hybridization in the same solution supplemented with 50 µCi 32-P-dCTP labelled probe for 18 h at ~40° C. and washing three times in 2×SSC, 0.2% SDS at 40° C. for 30 minutes). More specifically, the term is intended to refer to a DNA sequence which is at least 70% homologous to any of the sequences shown above encoding an endoglucanase of the invention, such as at least 75%, at least 80%, at least 85%, at least 90% or even at least 95% with any of the sequences shown above. The term is intended to include modifications of any of the DNA sequences shown above, such as nucleotide substitutions which do not give rise to another amino acid sequence of the polypeptide encoded by the sequence, but which correspond to the codon usage of the host organism into which a DNA construct comprising any Of the DNA sequences is introduced or nucleotide substitutions which do give rise to a different amino acid sequence and therefore, possibly, a different protein structure which might give rise to an endoglucanase mutant with different properties than the native enzyme. Other examples of possible modifications are insertion of one or more nucleotides into the sequence, addition of one or more nucleotides at either end of the sequence, or deletion of one or more nucleotides at either end or within the sequence.

In a still further aspect, the invention relates to an enzyme exhibiting endoglucanase activity, which enzyme iv) is encoded by a DNA sequence comprising or included in the following partial sequence GACAGTAGCAATCCAGCATTAGCAT-
CAGCCGCTTTGTACACCATGAAGTTCAC-
CGTATTGGCA CTGCTTCTCTCCCAGGTGTGGGC-
GGCCCCTCAGGCAAACGCTCCTCCAAT-
TTTCTCTGGCTT GGTAGTAATGAGTCTGGCGCA-
GAGTTTGGCCAGGCCAACATCCCCGGT-
GTTCTGGG (SEQ ID No: 19)

or a sequence homologous thereto encoding a polypeptide with endoglucanase activity, and/or v) is immunologically reactive with an antibody raised against a highly purified endoglucanase encoded by the DNA sequence defined in iv) and derived from *Aspergillus aculeatus*, CBS 101.43.

In the following disclosure, the enzyme defined by properties iv) and v) is referred to as of Endoglucanase type IV (or for short Endoglucanase IV or EG IV).

In still further aspects, the present invention relates to an enzyme preparation useful for the degradation of plant cell wall components, said preparation being enriched in an enzyme exhibiting endoglucanase activity as described above, as well to various uses of said enzyme preparation.

DETAILED DESCRIPTION OF THE INVENTION

Endoglucanase type II of the present invention has been found to have a surprisingly high specificity for xyloglucan and a very high Specific activity towards this substrate.

Endoglucanase type II of the present invention is preferably one which has a XGU/BGU, XGU/CMU and/or XGU/AVIU ratio (as defined above) of more than 50, such as 75, 90 or 100.

Furthermore, the endoglucanase type II is preferably substantially devoid of activity towards β-glucan and/or exhibits at the most 3% such as at the most 2% or about 1% activity towards carboxymethyl cellulose and/or Avicell when the activity towards xyloglucan is 100%. In addition, endoglucanase type II of the invention is preferably substantially devoid of transferase activity, an activity which has been observed for most xyloglucan specific endoglucanases of plant origin.

As will be apparent from the following examples an endoglucanase of type II of the present invention may be obtained from the fungal species *A. aculeatus*. Microbial endoglucanases with endoglucanase II type specificity has not previously been described. Xyloglucan specific endoglucanases from plants have been described, but these enzymes have transferase activity and therefore must be considered inferior to microbial xyloglucan specific endoglucanases whenever extensive degradation of xyloglucan is desirable. An additional advantage of a microbial enzyme is that it, in general, may be produced in higher amounts in a microbial host, than enzymes of other origins.

In one embodiment of the invention endoglucanase of type IV exhibits only low activity towards xyloglucan. In particular, endoglucanase type IV may be substantially devoid of xyloglucan degrading activity. Furthermore, endoglucanase of type IV exhibits a surprisingly high specificity and specific activity towards β-glucan.

An enzyme of the invention may be isolated by a general method involving cloning, in suitable vectors, a DNA library from Aspergillus spp., transforming suitable yeast host cells with said vectors, culturing the host cells under suitable conditions to express any enzyme of interest encoded by a clone in the DNA library, and screening for positive clones by determining any endoglucanase activity of the enzyme produced by such clones.

A more detailed description of this screening method is given in Example 1 below.

The DNA sequence coding for the enzyme may for instance be isolated by screening a cDNA library of *Aspergillus aculeatus*, e.g strain CBS 101.43, publicly available from Centraalbureau voor Schimmelcultures, and selecting for clones expressing the appropriate enzyme activity (i.e. endoglucanase activity as defined by the ability of the enzyme to hydrolyse β-1,3 and/or β-1,4 bonds between two glucose molecules in polymers containing glucose (e.g. cellulose, cereal β-glucans or xyloglucans). The appropriate DNA sequence may then be isolated from the clone by standard procedures, e.g. as described in Example 1. It is expected that a DNA sequence coding for a homologous enzyme may be derived by similarly screening a cDNA library of another microorganism, in particular a fungus, such as a strain of Aspergillus, in particular *A. aculeatus* or *A. niger*, a strain of Trichoderma, in particular *T. harzianum, T. reesie*, a strain of Fusarium, in particular *F. oxysporum* or a strain of Humicola.

Alternatively, the DNA coding for an endoglucanase of the invention may, in accordance with well-known procedures, conveniently be isolated from DNA from any of the above mentioned organisms by use of oligonucleotide probes, such as 20 mer probes, prepared on the basis of a DNA sequence disclosed herein. For instance, a suitable oligonucleotide probe may, e.g., be prepared on the basis of any of the partial nucleotide sequences a)–p) listed above.

The DNA sequence may subsequently be inserted into a recombinant expression vector. This may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the vector, the DNA sequence encoding the endoglucanase should be operably connected to a suitable promoter and terminator sequence. The promoter may be any DNA sequence which shows transcriptional activity in the host cell of choice and may be derived from genes encoding proteins either homologous or heterologous to the host cell. The procedures used to ligate the DNA sequences coding for the endoglucanase, the promoter and the terminator, respectively, and to insert them into suitable vectors are well known to persons skilled in the art (cf., for instance, Sambrook et al., *Molecular Cloning. A Laboratory Manual*, Cold Spring Harbor, N.Y., 1989).

The host cell which is transformed with the DNA sequence encoding the enzyme of the invention is preferably a eukaryotic cell, in particular a fungal cell such as a yeast or filamentous fungal cell. In particular, the cell may belong to a species of Aspergillus, most preferably *Aspergillus oryzae* or *Aspergillus niger*. Fungal cells may be transformed by a process involving protoplast formation and transformation of the protoplasts followed by regeneration of the cell wall in a manner known per se. The use of Aspergillus as a host microorganism is described in EP 238 023 (of Novo Nordisk A/S), the contents of which are hereby incorporated by reference. The host cell may also be a yeast cell, e.g. a strain of Saccharomyces, in particular *Saccharomyces cerevisiae*.

In a still further aspect, the present invention relates to a method of producing an enzyme according to the invention, wherein a suitable host cell transformed with a DNA sequence encoding the enzyme is cultured under conditions permitting the production of the enzyme, and the resulting enzyme is recovered from the culture.

The medium used to culture the transformed host cells may be any conventional medium suitable for growing the host cells in question. The expressed endoglucanase may conveniently be secreted into the culture medium and may be recovered therefrom by well-known procedures including separating the cells from the medium by centrifugation or filtration, precipitating proteinaceous components of the medium by means of a salt such as ammonium sulphate, followed by chromatographic procedures such as ion exchange chromatography, affinity chromatography, or the like.

The thus purified endoglucanase may be employed for immunization of animals for the production of antibodies. More specifically, antiserum against the endoglucanase may be raised by immunizing rabbits (or other rodents) according to the procedure described by N. Axelsen et al. in: *A Manual of Quantitative Immunoelectrophoresis*, Blackwell Scientific Publications, 1973, Chapter 23, or A. Johnstone and R. Thorpe, *Immunochemistry in Practice*, Blackwell Scientific Publications, 1982 (more specifically pp. 27–31). Purified immunoglobulins may be obtained from the antisera, for example by salt precipitation (($NH_4)_2SO_4$), followed by dialysis and ion exchange chromatography, e.g. on DEAE-Sephadex. Immunochemical characterization of proteins may be done either by Outcherlony double-diffusion analysis (O. Ouchterlony in: *Handbook of Experimental Immunology* (D. M. Weir, Ed.), Blackwell Scientific Publications, 1967, pp. 655–706), by crossed immunoelectrophoresis (N. Axelsen et al., supra, Chapters 3 and 4), or by rocket immunoelectrophoresis (N. Axelsen et al., Chapter 2).

The endoglucanases according to the invention may be produced essentially free from other plant cell wall degrading enzymes. This makes it possible to use the enzymes alone or together with other enzymes, such as galactanases and xylanases, to give the optimal combination of enzymes for a particular application. It is thereby possible to design enzyme combinations, which only degrade specific parts of the plant cell. This specific degradation has not previously been possible to obtain with commercially available cellulase, hemicellulase and/or pectinase preparations.

The present invention provides endoglucanases of a wide specificity range. Thus, an endoglucanase of type II of the invention has been found to be highly specific to xyloglucan, whereas an endoglucanase of type IV has been found to degrade cellulose and cellulose derivatives like carboxymethylcellulose and hydroxyethylcellulose, and mixed β-1,3-1,4 glucans like cereal β-glucans. In fact, an endoglucanase type IV of the invention has been found to have a very high β-glucan degrading capability.

This makes the endoglucanases useful (either alone or in combination) in applications where modification or full or partial degradation of cellulose, xylo-glucans and mixed β-1,3-1,4 glucans or derivatives of these substrates are desired.

The activity towards mixed β-1,3-1,4 glucans makes EG IV and homologous thereof useful for brewing purposes as the enzymes degrades the barley β-glucan and thereby reduces the viscosity and improves the filterability of the wort. In brewing the high specificity for β-glucans is an advantage as compared to other endoglucanases as the viscosity caused by β-glucan can be reduced without simultaneous degradation of the cellulose structures which are essential for the filterability of the wort where brewers spent grains act as filter-aid. Finally, the activity towards mixed β-1,3-1,4 glucans makes the enzyme useful for addition to animal feed to improve the feed-uptake.

The activity of endoglucanase type II enzymes of the invention towards xyloglucans and the activity of endoglucanase type IV enzymes towards cellulose are useful for treatment of fruits and vegetables. The endoglucanases may for example be used in treatment of e.g. apple and pear mash for high yielding juice processes. The juices can be made clear or cloud-stable depending on the used combination of enzymes. The endoglucanses may be used in mash treatment of grapes for higher yields and better aroma and colour of wine. The endoglucanases may be used to facilitate pectin extraction from e.g. citrus peels, apples, or sugar beets and for purification of other industrial gums such as guar gum and locust bean gum, as the recombinant enzymes have the advantage that they may be produced free from pectinolytic enzymes or gum-degrading enzymes such as endomannanase.

The hemicellulose like xyloglucan has to be removed from plant fibres like cotton, flax, hemp and jute before these can be used for textiles. For this purpose endoglucanase of type II has the advantage that it specifically removes the xyloglucan without damaging the cellulose. This endoglucanase may be used alone or together with other enzymes (e.g. pectinases) active on the pectic substances on the fibres.

Furthermore, the endoglucanases of the invention and analogous thereof may be used to treat cellulose fibres or cellulose-fibre rich material. The endoglucanases may e.g. be used in the paper industry to improve the drainage of pulp, and to treat fabrics such as cotton fabrics, to give a more smooth fabric.

The endoglucanases of the invention may also be used to produce oligosaccharides from e.g. plant material with mixed β-1,3-1,4 glucan and xyloglucan. The resulting oligosaccharides may be used as bulking agents in e.g. food.

In accordance with the above, a preferred type of enzyme preparation of the invention is an enzyme preparation which is enriched in an endoglucanase according to the invention, e.g. an endoglucanase of type II and/or an endoglucanase of type IV, preferably with an enrichment factor of at least 1.1. In this manner a boosting of the cell wall degrading ability of the enzyme preparation can be obtained.

The enzyme preparation having been enriched with an enzyme of the invention may e.g. be an enzyme preparation comprising multiple enzymatic activities, in particular an enzyme preparation comprising multiple plant cell wall degrading enzymes such as Pectinex®, Pectinex Ultra SP®, Celluclast or Celluzyme (all available from Novo Nordisk A/S). In the present context, the term "enriched" is intended to indicate that the endoglucanase activity of the enzyme preparation has been increased, e.g. with an enrichment factor of 1.1, conveniently due to addition of an enzyme of the invention prepared by the method described above.

Alternatively, the enzyme preparation enriched in an enzyme exhibiting endoglucanase activity may be one which comprises an enzyme of the invention as the major enzymatic component, e.g. a mono-component enzyme preparation.

The enzyme preparation may be prepared in accordance with methods known in the art and may be in the form of a liquid or a dry preparation. For instance, the enzyme preparation may be in the form of a granulate or a microgranulate. The enzyme to be included in the preparation may be stabilized in accordance with methods known in the art.

The enzyme preparation of the invention may, in addition to an endoglucanase of the invention, contain one or more other plant cell wall degrading enzymes, for instance those with cellulytic, xylanolytic or pectinolytic activities such as xylanase, arabinanase, rhamnogalacturonase, pectin acetylesterase, galactanase, polygalacturonase, pectin lyase, pectate lyase, endoglucanase or pectin methylesterase. The additional enzyme(s) may be producible by means of a microorganism belonging to the genus Aspergillus, preferably Aspergillus niger, Aspergillus aculeatus, Aspergillus awamori or Aspergillus oryzae. Such a preparation is able to provide an extraordinary good total liquefaction power and thus a marked viscosity decrease of apple mash and similar biological materials.

It will be understood that an enzyme preparation may be used for the above mentioned purposes. In this respect, the dosage of the enzyme preparation of the invention and other conditions under which the preparation is used may be determined on the basis of methods known in the art.

The total liquefaction power of the enzyme preparation is determined as the decrease in total viscosity (=a function of serum+structural viscosity) in a finely milled apple mash when monitored continuously over 2 hours by means of a rotary viscosimeter.

BRIEF DESCRIPTION OF THE DRAWINGS

The invention is further described in the accompanying drawings, in which.

The invention is described in further detail in the following examples which are not in any way intended to limit the scope of the invention as claimed.

MATERIALS AND METHODS

Donor organism: mRNA was isolated from Aspergillus aculeatus, CBS 101.43, grown in a soy-containing fermentation medium with agitation to ensure sufficient aeration. Mycelia were harvested after 3–5 days' growth, immediately frozen in liquid nitrogen and stored at −80° C.

Yeast strains: The Saccharomyces cerevisiae strain used was yNG231 (MAT alpha, leu2, ura3–52, his4–539, pep4-delta 1, cir+) or JG169 (MATα; ura 3-52; leu 2-3, 112; his 3-D200; pep 4-113; prc1::HIS3; prb1:: LEU2; cir+).

Figure 1:
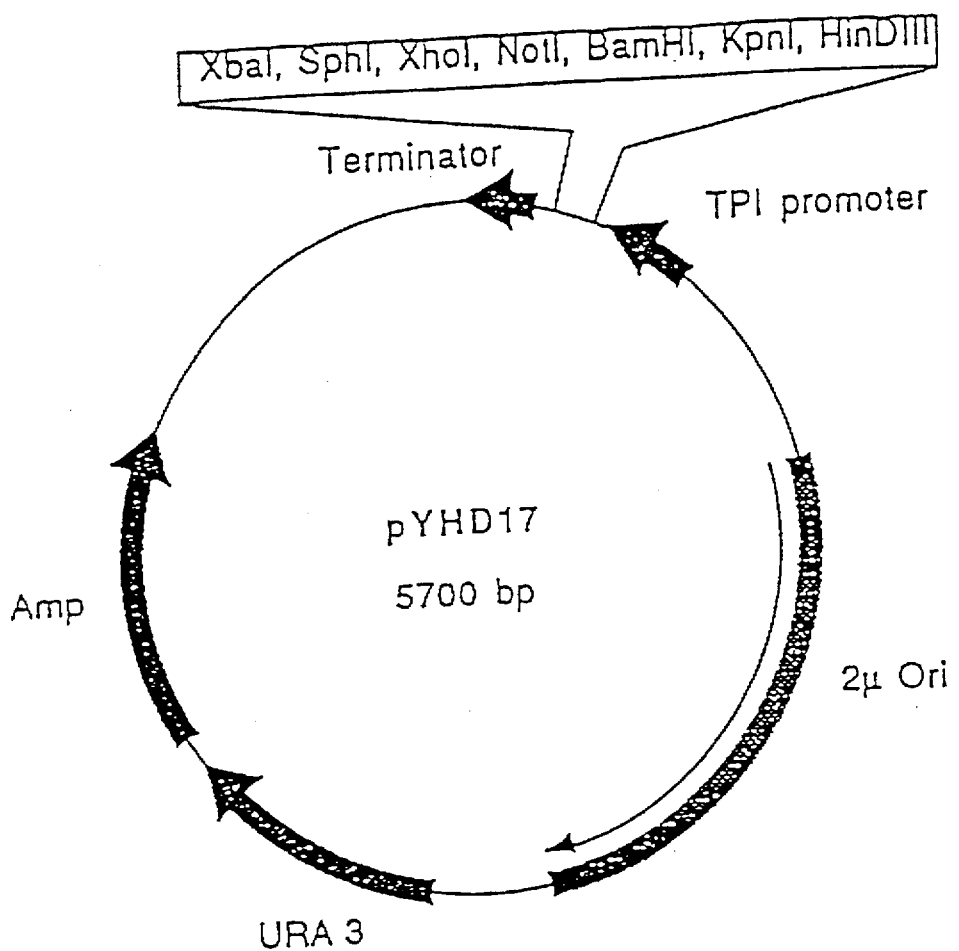
FIG. 1 is a restriction map of plasmid pYHD17.

Construction of an expression plasmid: The commercially available plasmid pYES II (Invitrogen) was cut with SpeI, filled in with Klenow DNA polymerase+dNTP and cut with ClaI. The DNA was size fractionated on an agarose gel, and a fragment of about 2000 bp was purified by electroelution. The same plasmid was cut with ClaI/PvuII, and a fragment of about 3400 bp was purified by electroelution. The two fragments were ligated to a blunt-ended SphI/EcoRI fragment containing the yeast TPI promoter. This fragment was isolated from a plasmid in which the TPI promoter from *S. cerevisiae* (cf. T. Albers and G. Kawasaki, J. Mol. Appl. Genet. 1, 1982, pp. 419–434) was slightly modified: an internal SphI site was removed by deleting the four bp constituting the core of this site. Furthermore, redundant sequences upstream of the promoter were removed by Ball exonuclease treatment followed by addition of a SphI linker. Finally, an EcoRI linker was added at position −10. After these modifications, the promoter is included in a SphI-EcoRI fragment. Its efficiency compared to the original promoter appears to be unaffected by the modifications. The resulting plasmid pYHD17 is shown in FIG. 1.

Preparation of RNase-free glassware, tips and solutions: All glassware used in RNA isolations was baked at 220° C. for at least 12 h. Eppendorf tubes, piper tips and plastic columns were treated in 0.1% diethylpyrocarbonate (DEPC) in EtOH for 12 h, and autoclaved. All buffers and water (except Tris-containing buffers) were treated with 0.1% DEPC for 12 h at 37° C., and autoclaved.

Extraction of total RNA: The total RNA was prepared by extraction with guanidinium thiocyanate followed by ultracentrifugation through a 5.7M CsCl cushion (Chirgwin et al., 1979) using the following modifications. The frozen mycelia were ground in liquid $N_2$ to fine powder with a mortar and a pestle, followed by grinding in a precooled coffee mill, and immediately suspended in 5 vols of RNA extraction buffer (4M GuSCN, 0.5% Na-laurylsarcosine, 25 mM Na-citrate, pH 7.0, 0.1M β-mercaptoethanol). The mixture was stirred for 30 min. at RT° and centrifuged (30 min., 5000 rpm, RT°, Heraeus Megafuge 1.0 R) to pellet the cell debris. The supernatant was collected, carefully layered onto a 5.7M CsCl cushion (5.7M CsCl, 0.1M EDTA, pH 7.5, 0.1% DEPC; autoclaved prior to use) using 26.5 ml supernatant per 12.0 ml CsCl cushion, and centrifuged to obtain the total RNA (Beckman, SW 28 rotor, 25 000 rpm, RT°, 24 h). After centrifugation the supernatant was carefully removed and the bottom of the tube containing the RNA pellet was cut off and rinsed with 70% EtOH. The total RNA pellet was transferred into an Eppendorf tube, suspended in 500 μl TE, pH 7.6 (if difficult, heat occasionally for 5 min at 65° C.), phenol extracted and precipitated with ethanol for 12 h at −20° C. (2.5 vols EtOH, 0.1 vol 3M NaAc, pH 5.2). The RNA was collected by centrifugation, washed in 70% EtOH, and resuspended in a minimum volume of DEPC-DIW. The RNA concentration was determined by measuring $OD_{260/280}$.

Isolation of poly(A)$^+$RNA: The poly(A)+RNAs were isolated by oligo(dT)-cellulose affinity chromatography (Aviv & Leder, 1972). Typically, 0.2 g of oligo(dT) cellulose (Boehringer Mannheim) was preswollen in 10 ml of 1× column loading buffer (20 mM Tris-Cl, pH 7.6, 0.5M NaCl, 1 mM EDTA, 0.1% SDS), loaded onto a DEPC-treated, plugged plastic column (Poly Prep Chromatography Column, Bio Rad), and equilibrated with 20 ml 1× loading buffer. The total RNA was heated at 65° C. for 8 min., quenched on ice for 5 min, and after addition of 1 vol 2× column loading buffer to the RNA sample loaded onto the column. The eluate was collected and reloaded 2–3 times by heating the sample as above and quenching on ice prior to each loading. The oligo(dT) column was washed with 10 vols of 1× loading buffer, then with 3 vols of medium salt buffer (20 mM Tris-Cl, pH 7.6, 0.1M NaCl, 1 mM EDTA, 0.1% SDS), followed by elution of the poly(A)$^+$ RNA with 3 vols of elution buffer (10 mM Tris-Cl, pH 7.6, 1 mM EDTA, 0.05% SDS) preheated to 65° C., by collecting 500 μl fractions. The $OD_{260}$ was read for each collected fraction, and the mRNA containing fractions were pooled and ethanol precipitated at −20° C. for 12 h. The poly(A)$^+$ RNA was collected by centrifugation, resuspended in DEPC-DIW and stored in 5–10 μg aliquots at −80° C.

Northern blot analysis: The poly(A)$^+$ RNAs (5 μg/sample) from various mycelia were electrophoresed in 1.2 agarose-2.2M formaldehyde gels (Sambrook et al., 1989) and blotted to nylon membranes (Hybond-N, Amersham) with 10× SSC (Sambrook et al., 1989) as transfer buffer. Three random-primed (Feinberg & Vogelstein, 1983) $^{32}$P-labeled cDNA probes were used in individual hybridizations: 1) a 1.3 kb Not I-Spe I fragment for polygalacturonase I from *A. aculeatus* (described in Danish Patent Application DK 1545/92), 2) a 1.3 kb Not I-Spe I fragment encoding endoglucanase I from *A. aculeatus* (as described in DK 0419/92) and 3) a 1.2 kb Eag I fragment for galactanase I from *A. aculeatus* (described in WO 92/13945). Northern hybridizations were carried out in 5× SSC (Sambrook et al., 1989), 5× Denhardt's solution (Sambrook et al., 1989), 0.5% SDS (w/v) and 100 μg/ml denatured salmon sperm DNA with a probe concentration of ca. 2 ng/ml for 16 h at 65° C. followed by washes in 5× SSC at 65° C. (2×15 min), 2× SSC, 0.5% SDS (1×30 min), 0.2× SSC, 0.5% SDS (1×30 min), and 5× SSC (2×15 min). After autoradiography at −80° C. for 12 h, the probe #1 was removed from the filter according to the manufacturer's instructions and rehybridized with probe #2, and eventually with probe #3. The RNA ladder from Bethesda Research Laboratories was used as a size marker.

cDNA synthesis First strand synthesis: Double-stranded cDNA was synthesized from 5 μg of *A. aculeatus* poly(A)$^+$ RNA by the RNase H method (Gubler & Hoffman 1983, Sambrook et al., 1989) using the hairpin modification. The poly(A)$^+$RNA (5 μg in 5 μl of DEPC-treated water) was heated at 70° C. for 8 min., quenched on ice, and combined in a final volume of 50 μl with reverse transcriptase buffer (50 mM Tris-Cl, pH 8.3, 75 mM KCl, 3 mM $MgCl_2$, 10 mM DTT, Bethesda Research Laboratories) containing 1 mM each dNTP (Pharmacia), 40 units of human placental ribonuclease inhibitor (RNasin, Promega), 10 μg of oligo(dT)$_{12-18}$ primer (Pharmacia) and 1000 units of SuperScript II RNase H- reverse transcriptase (Bethesda Research Laboratories). First-strand cDNA was synthesized by incubating the reaction mixture at 45° C. for 1 h.

Second strand synthesis: After synthesis 30 μl of 10 mM Tris-Cl, pH 7.5, 1 mM EDTA was added, and the mRNA:cDNAhybrids were ethanol precipitated for 12 h at −20° C. by addition of 40 μg glycogen carrier (Boehringer Mannheim) 0.2 vols 10M $NH_4Ac$ and 2.5 vols 96% EtOH. The hybrids were recovered by centrifugation, washed in 70% EtOH, air dried and resuspended in 250 μl of second strand buffer (20 mM Tris-Cl, pH 7.4, 90 mM KCl, 4.6 mM $MgCl_2$, 10 mM $(NH_4)_2SO_4$, 16 μM βNAD$^+$) containing 100 μM each dNTP, 44 units of *E. coli* DNA polymerase I (Amersham), 6.25 units of RNase H (Bethesda Research Laboratories) and 10.5 units of *E. coli* DNA ligase (New England Biolabs). Second strand cDNA synthesis was performed by incubating the reaction tube at 16° C. for 3 h, and the reaction was stopped by addition of EDTA to 20 mM final concentration followed by phenol extraction.

Mung bean nuclease treatment: The double-stranded (ds) cDNA was ethanol precipitated at −20° C. for 12 h by addition of 2 vols of 96% EtOH, 0.1 vol 3M NaAc, pH 5.2, recovered by centrifugation, washed in 70% EtOH, dried (SpeedVac), and resuspended in 30 μl of Mung bean nuclease buffer (30 mM NaAc, pH 4.6, 300 mM NaCl, 1 mM ZnSO4, 0.35 mM DTT, 2% glycerol) containing 36 units of Mung bean nuclease (Bethesda Research Laboratories). The single-stranded hair-pin DNA was clipped by incubating the reaction at 30° C. for 30 min, followed by addition of 70 μl 10 mM Tris-Cl, pH 7.5, 1 mM EDTA, phenol extraction, and ethanol precipitation with 2 vols of 96% EtOH and 0.1 vol 3M NaAc, pH 5.2 at −20° C. for 12 h.

Blunt-ending with T4 DNA polymerase: The ds cDNA was blunt-ended with T4 DNA polymerass in 50 μl of T4 DNA polymerass buffer (20 mM Tris-acetate, pH 7.9, 10 mM MgAc, 50 mM KAc, 1 mM DTT) containing 0.5 mM each dNTP and 7.5 units of T4 DNA polymerase (Invitrogen) by incubating the reaction mixture at 37° C. for 15 min. The reaction was stopped by addition of EDTA to 20 mM final concentration, followed by phenol extraction and ethanol precipitation.

Adaptor ligation and size selection: After the fill-in reaction the cDNA was ligated to non-palindromic BstX I adaptors (1 μg/μl, Invitrogen) in 30 μl of ligation buffer (50 mM Tris-Cl, pH 7.8, 10 mM MgCl2, 10 mM DTT, 1 mM ATP, 25 μg/ml bovine serum albumin) containing 600 pmol BstX I adaptors and 5 units of T4 ligase (Invitrogen) by incubating the reaction mix at 16° C. for 12 h. The reaction was stopped by heating at 70° C. for 5 min, and the adapted cDNA was size-fractionated by agarose gel electrophoresis (0.8% HSB-agarose, FMC) to separate unligated adaptors and small cDNAs. The cDNA was size-selected with a cut-off at 0.7 kb, and the cDNA was electroeluted from the agarose gel in 10 mM Tris-Cl, pH 7.5, 1 mM EDTA for 1 h at 100 volts, phenol extracted and ethanol precipitated at −20° C. for 12 h as above.

Construction of cDNA libraries: The adapted, ds cDNA was recovered by centrifugation, washed in 70% EtOH and resuspended in 25 ml DIW. Prior to large-scale library ligation, four test ligations were carried out in 10 μl of ligation buffer (same as above) each containing 1 μl ds cDNA (reaction tubes #1–#4), 2 units of T4 ligase (Invitrogen) and 50 ng (tube #1), 100 ng (tube #2) and 200 ng (tubes #3 and #4) Bst XI cleaved yeast expression vector either pYES 2.0 vector Invitrogen or yHD13). The ligation reactions were performed by incubation at +16° C. for 12 h, heated at 70° C. for 5 min, and 1 μl of each ligation electroporated (200 Ω, 2.5 kV, 25 μF) to 40 μl competent E. coli 1061 cells (OD600=0.9 in 1 liter LB-broth, washed twice in cold DIW, once in 20 ml of 10% glycerol, resuspended in 2 ml 10% glycerol). After addition of 1 ml SOC to each transformation mix, the cells were grown at 37° C. for 1 h, 50 μl plated on LB+ampicillin plates (100 μg/ml) and grown at 37° C. for 12 h.

Using the optimal conditions a large-scale ligation was set up in 40 μl of ligation buffer containing 9 units of T4 ligase, and the reaction was incubated at 16° C. for 12 h. The ligation reaction was stopped by heating at 70° C. for 5 min, ethanol precipitated at −20° C. for 12 h, recovered by centrifugation and resuspended in 10 μl DIW. One μl aliquots were transformed into electrocompetent E. coli 1061 cells using the same electroporation conditions as above, and the transformed cells were titered and the library plated on LB+ampicillin plates with 5000–7000 c.f.u./plate. To each plate was added 3 ml of medium. The bacteria were scraped off, 1 ml glycerol was added and stored at −80° C. as pools. The remaining 2 ml were used for DNA isolation. If the amount of DNA was insufficient to give the required number of yeast transformants, large scale DNA was prepared from 500 ml medium (TB) inoculated with 50 μl of −80° C. bacterial stock propagated overnight.

Construction of yeast libraries: To ensure that all the bacterial clones were tested in yeast, a number of yeast transformants 5 times larger than the number of bacterial clones in the original pools was set as the limit.

One μl aliquots of purified plasmid DNA (100 ng/μl) from individual pools were electroporated (200 Ω, 1.5 kV, 25 μF) into 40 μl competent S. cerevisiae JG 169 cells (OD600=1.5 in 500 ml YPD, washed twice in cold DIW, once in cold 1M sorbitol, resuspended in 0.5 ml 1M sorbitol, Becker & Guarante, 1991). After addition of 1 ml 1M cold sorbitol, 80 μl aliquots were plated on SC+glucose−uracil to give 250–400 c.f.u./plate and incubated at 30° C. for 3–5 days.

Figure 2:
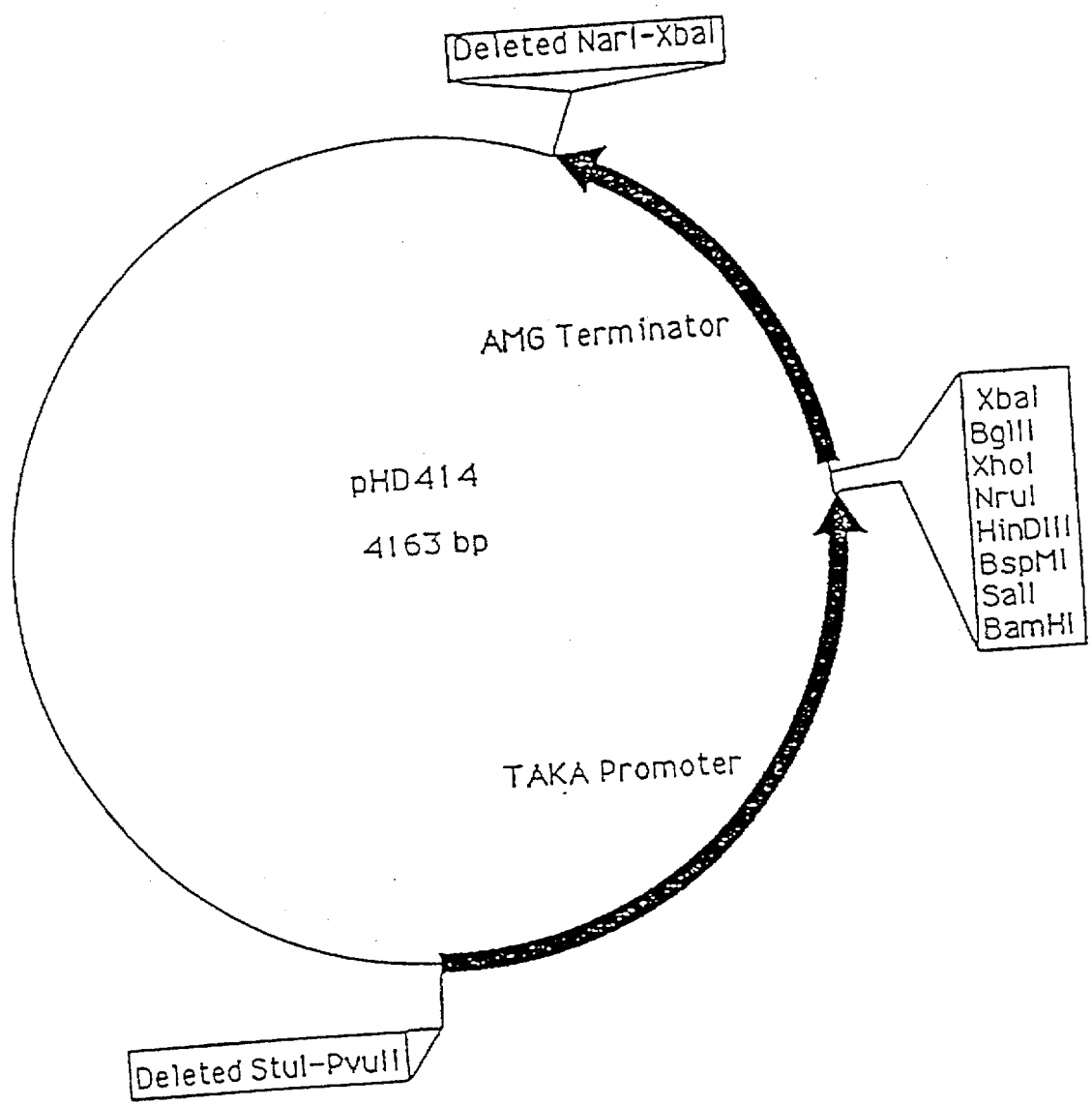
FIG. 2 a restriction map of plasmid pHD 414.

Construction of an Aspergillus expression vector: the vector pHD414 is a derivative of the plasmid p775 (described in EP 238 023). In contrast to this plasmid, pHD 414 has a string of unique restriction sites between the promoter and the terminator. The plasmid was constructed by removal of an approximately 200 bp long fragment (containing undesirable RE sites) at the 3'end of the terminator, and subsequent removal of an approximately 250 bp long fragment at the 5'end of the promoter, also containing undesirable sites. The 200 bp region was removed by cleavage with NarI (positioned in the pUC vector) and XbaI (just 3' to the terminator), subsequent filling in the generated ends with Klenow DNA polymerase +dNTP, purification of the vector fragment on gel and religation of the vector fragment. This plasmid was called pHD413. pHD413 was cut with StuI (positioned in the 5'end of the promoter) and PvuII (in the pUC vector), fractionated on gel and religated. The plasmid pHD 414 is shown in FIG. 2 which is a map of plasmid pHD414, wherein "AMG Terminator" indicates the A. niger glucoamylase terminator, and "TAKA Promoter" indicates the A. oryzae TAKA amylase promoter.

Transformation of Aspergillus oryzae or Aspergillus niger (general procedure)

100 ml of YPD (Sherman et al., Methods in Yeast Genetics, Cold Spring Harbor Laboratory, 1981) is inoculated with spores of A. oryzae or A. niger and incubated with shaking at 37° C. for about 2 days. The mycelium is harvested by filtration through miracloth and washed with 200 ml of 0.6M MgSO$_4$. The mycelium is suspended in 15 ml of 1.2M MgSO$_4$, 10 mM NaH$_2$PO$_4$, pH=5.8. The suspension is cooled on ice and 1 ml of buffer containing 120 mg of Novozym®234, batch 1687 is added. After 5 minutes 1 ml of 12 mg/ml BSA (Sigma type H25) is added and incubation with gentle agitation continued for 1.5–2.5 hours at 37° C. until a large number of protoplasts is visible in a sample inspected under the microscope.

The suspension is filtered through miracloth, the filtrate transferred to a sterile tube and overlayered with 5 ml of 0.6M sorbitol, 100 mM Tris-HCl, pH=7.0. Centrifugation is performed for 15 minutes at 100 g and the protoplasts are collected from the top of the MgSO$_4$ cushion. 2 volumes of STC (1.2M sorbitol, 10 mM Tris-HCl, pH=7.5, 10 mM CaCl$_2$) are added to the protoplast suspension and the mixture is centrifuged for 5 minutes at 1000 g. The protoplast pellet is resuspended in 3 ml of STC and repelleted. This is repeated. Finally the protoplasts are resuspended in 0.2–1 ml of STC.

100 μl of protoplast suspension is mixed with 5–25 μg of the appropriate DNA in 10 μl of STC. Protoplasts are mixed with p3SR2 (an A. nidulans amdS gene carrying plasmid). The mixture is left at room temperature for 25 minutes. 0.2 ml of 60% PEG 4000 (BDH 29576), 10 mM CaCl$_2$ and 10 mM Tris-HCl, pH=7.5 is added and carefully mixed (twice) and finally 0.85 ml of the same solution is added and carefully mixed. The mixture is left at room temperature for 25 minutes, spun at 2500 g for 15 minutes and the pellet is resuspended in 2 ml of 1.2M sorbitol. After one more sedimentation the protoplasts are spread on the appropriate plates. Protoplasts are spread on minimal plates (Cove Biochem. Biophys.Acta 113 (1966) 51–56) containing 1.0M sucrose, pH=7.0, 10 mM acetamide as nitrogen source and 20 mM CsCl to inhibit background growth. After incubation for 4–7 days at 37° C. spores are picked and spread for single colonies. This procedure is repeated and spores of a single colony after the second reisolation is stored as a defined transformant.

Media

YPD: 10 g yeast extract, 20 g peptone, $H_2O$ to 810 ml. Autoclaved, 90 ml 20% glucose (sterile filtered) added.

YPG-agar: 25 g/l Bactoagar, 15 g/l glucose, 5 g/l $K_2PO_4$, 0.5 g/l $MgSO_4$-$7H_2O$, pH adjusted to 5.0. Autoclaved.

10× Basal salt: 66.8 g yeast nitrogen base, 100 g succinic acid, 60 g NaOH, $H_2O$ ad 1000 ml, sterile filtered.

SC-URA: 90 ml 10× Basal salt, 22.5 ml 20% casamino acids, 9 ml 1% tryptophane, $H_2O$ ad 806 ml, autoclaved, 3.6 ml 5% threonine and 90 ml 20% glucose added.

SC-H agar: 7.5 g/l yeast nitrogen base without amino acids, 11.3 g/l succinic acid, 6.8 g/l NaOH, 5.6 g/l casamino acids without vitamins, 0.1 g/l tryptophan and 20 g/l agar (Bacto). Autoclaved for 20 min. at 121° C. After autoclaving, 55 ml of a 22% galactose solution and 118 ml of a 5% threonine solution were added per 450 ml agar.

YNB-1 agar: 3.3 g/l $KH_2PO_4$, 16.7 g/l agar, pH adjusted to 7. Autoclaved for 20 min. at 121° C. After autoclaving, 25 ml of a 13.6% yeast nitrogen base without amino acids, 25 ml of a 40% glucose solution, 1.5 ml of a 1% L-leucine solution and 1.5 ml of a 1% histidine solution were added per 450 ml agar.

YNB-1 broth: Composition as YNB-1 agar, but without the agar. FG-4-Agar: 35 g/l agar, 30 g/l Soy bean meal, 15 g/l maltodextrin (Glucidex 6), 5 g/l Bacto pepton, pH 7. Autoclaved 40 min at 121° C.

FG-4 medium: 30 g/l Soy bean meal, 15 g/l maltodextrin (Glucidex 6), 5 g/l Bacto pepton. Autoclaved 40 min at 121° C.

AZCL xyloglucan: available from Megazyme, Australia.

AZCL-HE cellulose: available from Megazyme, Australia.

Characterization of an enzyme of the invention

SDS-PAGE Electrophoresis: SDS-PAGE electrophoresis was performed in a Mini-Leak 4 electrophoresis unit (Kem-En-Tec, Copenhagen) as a modified version of the Laemli procedure (Laemmli, 1970; Christgau, 1991). Briefly, the separation gel was cast with 12% acrylamide; 0.2% BIS acrylamide; 0.1% SDS; 0.375M Tris pH 8.8; 0.04% APS (ammonium-persulphate) & 0.04% TEMED. After 6–15 hours of polymerization the stacking gel was cast with 4.5% w/w Acrylamide; 0.075% BIS-acrylamide; 0.1% SDS; 66.5 mM Tris pH 6.8; 0.4% w/w APS (ammonium persulphate) & 0.4% TEMED. The electrode chambers are filled with running buffer: 25 mM Tris-base; 0.192M glycine & 0.05% SDS, whereafter the samples containing sample buffer are loaded, and the gel is run at 2–4 mA/gel for over-night running and 10–30 mA/gel for fast running. The gel is subsequently removed and stained by either commassie or silver staining.

Isoelectric focusing: Isoelectric focusing is carried out on Ampholine PAG plates pH 3.5–9.5 (Pharmacia, Upsala) on a Multiphor electrophoresis unit according to the manufactures instructions. After electrophoresis the gel is either commassie stained or silver stained.

Commassie and silver staining: The gel is carefully removed from the glass plates and incubated on a slowly rotating shaking table in approximately 100 ml of the following solutions:

Coomassie staining:
1) 30 min in 40% v/v ethanol; 5% v/v acetic acid
2) 30 min in 40% v/v ethanol; 5% v/v acetic acid+0.1% Commassie R250
3) Destaining in 30 min in 40% v/v ethanol; 5% v/v acetic acid until background is sufficiently reduced.
4) Finally the gel is incubated in preserving solution: 5% v/v acetic acid; 10% v/v ethanol; 5% v/v glycerol and air dried between two sheets of cellophane membrane.

Silver staining:
1) 30 min in 40% v/v ethanol; 5% v/v acetic acid
2) 20 min in 10% v/v ethanol; 5% v/v acetic acid
3) 20 min in 0.0057% w/v APS (0.25 mM)
4) 60 min in 0.1% w/v $AgNO_3$
5) For development, the gel is dipped in developer: 0.015% formaldehyde; 2% w/v $Na_2CO_3$ for 30–60 sec. Then the gel is incubated in a second round of developer until satisfactory staining of the proteins has been achieved (5–15 min.). Finally the gel is incubated in preserving solution: 5% v/v acetic acid; 10% v/v ethanol; 5% v/v glycerol and air dried between two sheets of cellophane membrane.

Standard incubations: For characterization of the enzymes, incubations are carried out in Eppendorf tubes comprising 1 ml of substrate (AZCL-substrates or pure polysaccharides from MegaZyme). 0.5 ml 0.4% AZCL-substrate suspension is mixed with 0.5 ml 0.1M citrate/phosphate buffer of optimal pH and 10 µl of a suitably diluted enzyme solution is added. Incubations are carried out in Eppendorf Thermomixers for 15 minutes at 30° C. (if not otherwise specified).before heat-inactivation for 20 minutes at 95° C. Enzyme incubations are carried out in triplicate. A blank is produced in which enzyme is added but inactivated immediately. After centrifugation the absorbance of the supernatant is measured in microtiter plates at 620 nm and the blank is subtracted.

The activities of the enzymes are measured on different pure polysaccharides: xyloglucan and β-glucan from MegaZyme, CMC (Blanose from Aqualon) and Avicell (microcrystaline cellulose from Merck). Before use Avicell is swelled in 85% orthophosphoric acid for 1 hour at room temperature and washed with acetone and water. 0.5% solutions/suspensions of the different substrates are made in 0.1M acetate buffer (if not otherwise specified) of the optimal pH, 10 µl enzyme solutions are added to 1 ml of substrate, incubations are carried at 30° C. for 15 minutes before heat-inactivation as above. Reducing sugars are determined by reaction, in microtiter plates, with a PHBAH reagent comprising 0.15 g of para hydroxy benzoic acid hydrazide (Sigma H-9882), 0.50 g of potassium-sodium tartrate (Merck 8087) and 2% NaOH solution up to 10.0 ml. Results of blanks are subtracted. Glucose is used as a standard.

pH optimum is measured on substrates from MegaZyme (EG II on AZCL-xyloglucan, EG III on pure β-glucan, and EG IV on AZCL-β-glucan). 0.5 ml of 0.4% substrate is mixed with 0.5 ml 0.1M citrate/phosphate buffer of varying pH and 10 µl of a suitably diluted enzyme solution is added. Incubations are carried out as described above.

The specificity of the different endoglucanases on the different AZCL-substrates is tested as above at optimal pH in 0.1M acetate buffer.

pH stability is measured by leaving the enzyme for 1 hour in 0.1M citric acid/tri sodium phosphate buffers of varying pH before the enzyme is used for incubation of AZCL-β-glucan at the optimal pH.

Temperature optimum is measured by incubating the enzyme with AZCL-β-glucan substrate at varying temperatures for 15 minutes at the optimal pH.

Temperature stability is measured by leaving the enzyme, diluted in water, at various temperatures for 1 hour before incubation at 30° C. with the relevant substrate.

Km and specific activity are measured by carrying out incubations at substrate concentrations (S) ranging from 0.025 to 1.5% (xyloglucan for EG II and β-glucan for EG IV), measure the reaction rate (v), picture S/v as a function of S, carry out linear regression analysis, finding the slope (=1/Vmax) and the intercept (Km/Vmax) and calculating Km and the specific activity (=Vmax/E), where E is the amount of enzyme added.

For gel filtration chromatography 1% solutions/suspensions of the above mentioned pure polysaccharides are made. A suitable amount of enzyme is added and incubations are carried out for 0, 1, 2, 4 and 24 hours before heat-inactivation. 25 µl of sample is injected into three TSK-columns in a row (PW G4000, PW G3000, PW G2500) and saccharides are eluted with 0.4M acetate buffer pH 3.0 at 0.8 ml/min. Eluting saccharides are determined by a Shimadzu RI detector and data are collected and processed by Dionex software. Dextrans (from Sersa) are used as molecular weight standards.

EXAMPLES

Example 1

A library from Aspergillus aculeatus CBS 101.43 consisting of approx. $1.5 \times 10^6$ individual clones in 50 pools was constructed in *E. coli* as previously described.

DNA was isolated from 20 individual clones from the library and subjected to analysis for cDNA insertion. The insertion frequency was found to be >90% and the average insert size was approximately 1400 bp.

DNA from some of the pools was transformed into yeast, and 50–100 plates containing 200–500 yeast colonies were obtained from each pool. The colonies were scraped off and stored in glycerol at −80° C.

Yeast cells from the library were spread onto YNB agar to a total of about 250,000 colonies. The number of colonies per plate varied from 250 to 500. After 3–5 days of growth, the agar plates were replica plated onto several sets of SC-H agar plates and three different endoglucanases were identified:

One set of the replica plates contained 0.1% AZCL xyloglucan (Megazyme). These plates were incubated for 2–4 days at 30° C. Endoglucanase II and Endoglucanase III positive colonies were identified as colonies surrounded by a blue halo.

Another set of replica plates contained 0.1% AZCL-HE cellulose. These plates were incubated for 2–4 days at 30° C. Endoglucanase III and Endoglucanase IV positive colonies were indentified as colonies surrounded by a blue halo.

Cells from enzyme-positive colonies were spread for single colony isolation on agar, and an enzyme-producing single colony was identified and selected by the above described methods.

Characterization of positive clones: The positive clones were obtained as single colonies, the cDNA inserts were amplified directly from the yeast colony using biotinylated polylinker primers, purified by magnetic beads (Dynabead M-280, Dynal) system and characterized individually by sequencing the 5'-end of each cDNA clone using the chain-termination method (Sanger et al., 1977) and the Sequenase system (United States Biochemical). The partial DNA sequence of the enzyme gene obtained from screening with AZCL xyloglucan is shown in claim 2 and the partial DNA sequence of the enzyme gene obtained from screening with AZCL-HE cellulose is shown in claim 6. A partial DNA sequence was obtained for Endoglucanase III. This sequence was found to exhibit a substantial homology with the sequence disclosed by Ooi et al. 1990. Endoglucanase III is included in the following examples in order to illustrate the difference existing between the endoglucanases of the present invention and a prior art endoglucanase.

Example 2

Isolation of DNA DNA was isolated from two different isolates by the following general procedure:

The isolate was inoculated into 20 ml YNB-1 broth in a 50 ml glass test tube. The tube was shaken for 2 days at 30° C. The cells were harvested by centrifugation for 10 min. at 3000 rpm.

The cells were resuspended in 1 ml 0.9M sorbitol, 0.1M EDTA, pH 7.5. The pellet was transferred to an Eppendorf tube, and spun for 30 seconds at full speed. The cells were resuspended in 0.4 ml 0.9M sorbitol, 0.1M EDTA, 14 mM β-mercaptoethanol. 100 µl 2 mg/ml Zymolase was added, and the suspension was incubated at 37° C. for 30 minutes and spun for 30 seconds. The pellet (spheroplasts) was resuspended in 0.4 ml TE. 90 µl of (1.5 ml 0.5M EDTA pH 8.0, 0.6 ml 2M Tris-Cl pH 8.0, 0.6 ml 10% SDS) was added, and the suspension was incubated at 65° C. for 30 minutes. 80 µl 5M KOAc was added, and the suspension was incubated on ice for at least 60 minutes and spun for 15 minutes at full speed. The supernatant was transferred to a fresh tube which was filled with EtOH (room temp.) followed by thorough but gentle mixing and spinning for 30 seconds. The pellet was washed with cold 70% EtOH, spun for 30 seconds and dried at room temperature. The pellet was resuspended in 50 µl TE (Tris-EDTA) and spun for 15 minutes. The supernatant was transferred to a fresh tube. 2.5 µl 10 mg/ml RNase was added, followed by incubation at 37° C. for 30 minutes and addition of 500 µl isopropanol with gentle mixing. The mixture was spun for 30 seconds, and the supernatant was removed. The pellet was rinsed with cold 96% EtOH and dried at room temperature. The DNA was dissolved in 50 µl water to a final concentration of approximately 100 µl/ml.

The DNA was transformed into *E. coli* by standard procedures. Two *E. coli* colonies were isolated and analysed with the restriction enzymes HindIII and XbaI which excised the DNA insert.

The DNA sequences of several of the positive clones were determined. A partial DNA sequence of the gene encoding endoglucanase II of the invention is shown in SEQ ID NO:18 and a partial DNA sequence of the gene encoding endoglucanase IV of the invention is shown in SEQ ID NO:19.

Example 3

Expression of endoglucanase

In order to express an endoglucanase of the invention the DNA encoding the endoglucanase is digested with HindIII/XbaI, size fractionated on gel, and a fragment corresponding to the endoglucanase gene is purified. The gene is subsequently ligated to HindIII/XbaI digested pHD414 resulting in the plasmids pAEG II and pAEG IV.

After amplification of the DNA in E. coli the plasmids pAEG II and pAEG IV are transformed into Aspergillus oryzae as described above.

Each of the transformants was inoculated on FG agar in the centre of a Petri dish. After 4 days of incubation at 30° C. 4 mm diameter plugs were removed by means of a corkscrew.

One set of plugs was embedded in a xyloglucan overlayer gel containing 0.1% AZCL xyloglucan and 1% agarose in a buffer with an appropriate pH, and incubated overnight at 30° C. The endoglucanase II and endoglucanase III activity, respectively, was identified as described above. The best transformant had a halo with a diameter significantly larger than the A. oryzae background. This demonstrates efficient expression of endoglucanase II in A. oryzae.

Another set of plugs was embedded in a HE-cellulose overlayer gel containing 0.1% AZCL-HE cellulose and 1% agarose in a buffer with an approprioate pH, and incubated overnight at 30° C. The endoglucanase III and Endoglucanase IV activity, respectively, was identified as described above. The best transformant had a halo with a diameter significantly larger than the A. oryzae background. This demonstrates efficient expression of endoglucanase IV in A. oryzae.

Fed batch fermentation

Subsequently, EG II, EG III and EG IV, respectively, were produced by fed batch fermentation of A. oryzae expressing the enzymes. The medium used for the fermentation comprised maltodextrin as a carbon source, urea as a nitrogen source and yeast extract.

The fed batch fermentation was performed by innoculating a shake flask culture of the A. oryzae host cells in question into a medium comprising 3.5% of the carbon source and 0.5% of the nitrogen source. After 24 hours of cultivation at pH 5.0 and 34° C. the continuous supply of additional carbon and nitrogen sources were initiated. The carbon source was kept as the limiting factor and it was secured that oxygen was present in excess. The fed batch cultivation was continued for 4 days, after which the enzymes could be recovered.

Example 4

Characterization of Endoglucanase II and IV
Purification of EG II

The culture supernatant from fermentation of Aspergillus oryzae expressing the recombinant enzyme was centrifuged at 5000 xg and filtered through a 0.2 μm filter to remove the mycelia. 35–50 ml of the filtered supernatant were ultrafiltrated in a Filtron ultracette or Amicon ultrafiltration device with a 10 kDa membrane to achieve 10 fold concentration. This concentrate was diluted 100 times in 20 mM Tris pH 7.0 in two successive rounds of ultrafiltration in the same device. This ultrafiltrated sample was loaded at 2 ml/min on a Pharmacia HR16/10 Fast Flow Q Sepharose anion exchanger equilibrated in 20 mM Tris pH 7.0. After the sample had been applied, the column was washed with two column volumes 20 mM Tris pH 7.0, and bound proteins were eluted with a linear increasing NaCl gradient from 0 to 0.4M NaCl in 20 mM Tris pH 7.0.

The protein elutes at approx. 50 mM NaCl. The molecular weight of the enzyme was determined to about 35 kDa by SDS-PAGE and the isoelectric point to 3.4 by IEF.

The purified enzyme is used for characterization
Purification of endoglucanase III The culture supernatant from fermentation of Aspergillus oryzae expressing the recombinant enzyme (the expression level should be at least 0.5 mg enzyme/ml supernatant) was centrifuged at 5,000 xg for 20 min and filtered through a 0.2 μm filter to remove the mycelia. 35–50 ml of the filtered supernatant was ultrafiltrated in a Amicon YM03 ultrafiltration device with a 3 kDa membrane to achieve 10 fold concentration. This concentrate is diluted 100 times in 20 mM Tris pH 8.0 in two successive rounds of ultrafiltration in the same device. This ultrafiltratred sample is loaded at 1.5 ml/min on a Pharmacia HR16/10 Fast Flow Q Sepharose anion exchanger equilibrated in 20 mM Tris pH 8.0. After the sample has been applied, the Endoglucanase III is washed through the column, whereas the contraminating impurities remains bound to the column. The Endoglucanase III in this fraction is more than 95% pure.

The molecular weight of the enzyme was determined to about 26 kDa by SDS-PAGE and the isoelectric point to 5.5 by IEF.

The purified enzyme is used for characterization. For EG IV the fermentation supernatant is used for characterization.

pH optimum

Figure 3:
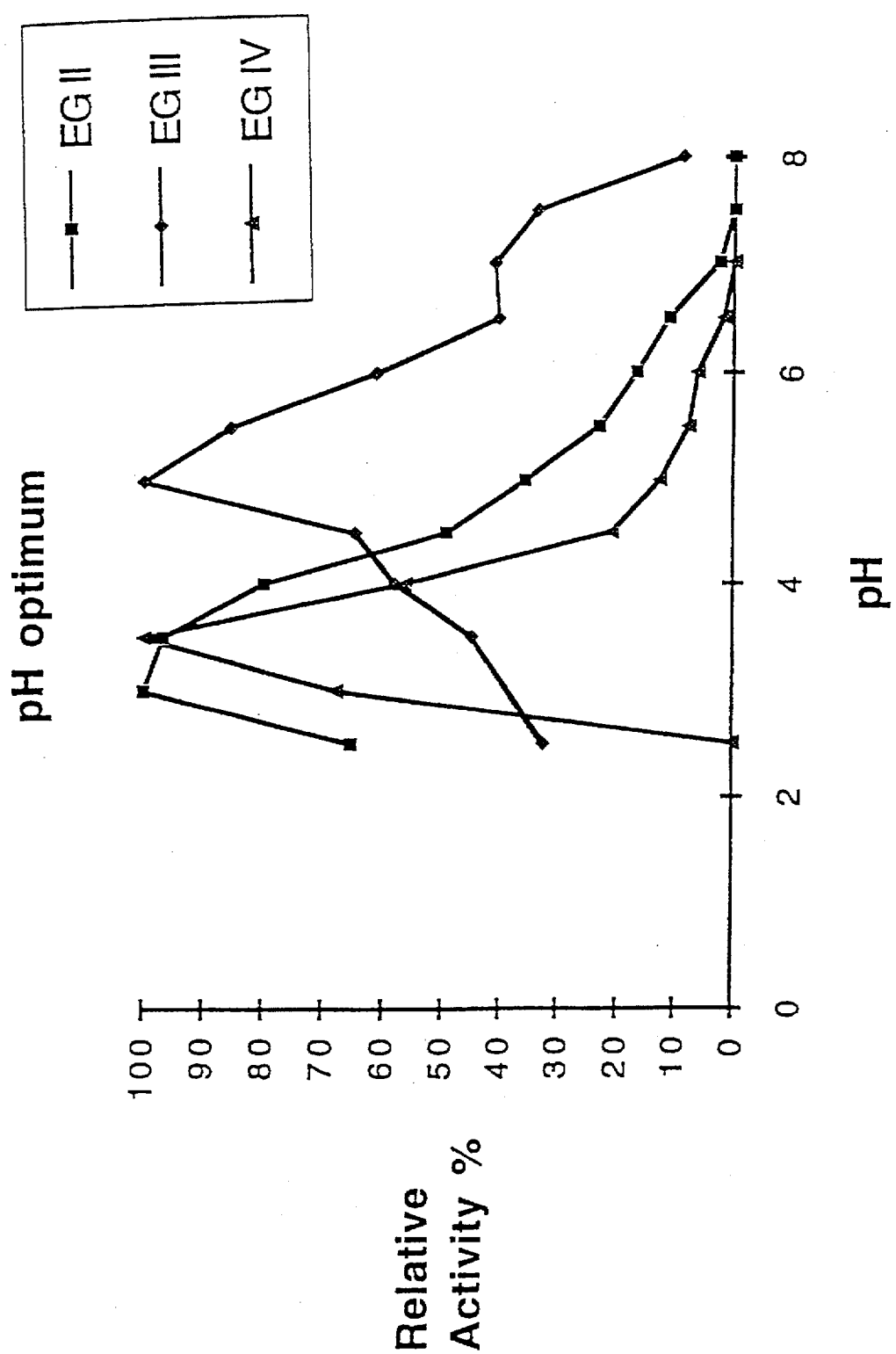
FIG. 3 illustrates the pH optimums for EG II, EG III and EG IV measured in citrate/phosphate buffers. The optimal activity for each enzyme is defined as 100%, FIG. 4 the pH stability for for EG II and EG III measured as the remaining activity after 1 h at different pH values compared to the activity of fresh enzyme (100%), FIG. 5 the temperature optimum for EG II and EG III. The optimal temperature for each enzyme is defined as 100%, and FIG. 6 The temperature stability of EG II and EG III measured as the remaining activity after preincubation in water for 1 h at different temperatures compared to the activity of fresh enzyme (100%).
Figure 4:
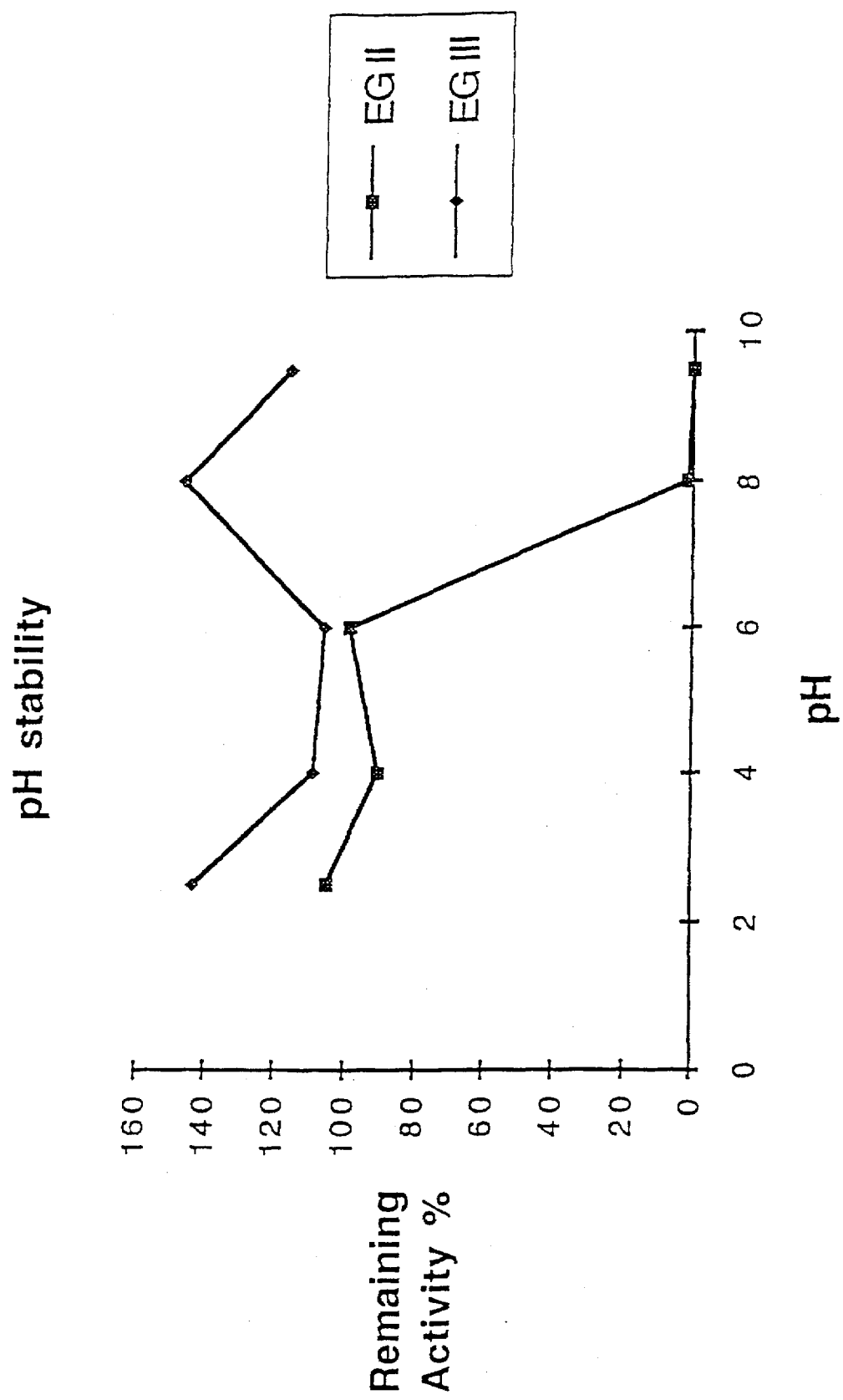
Figure 5:
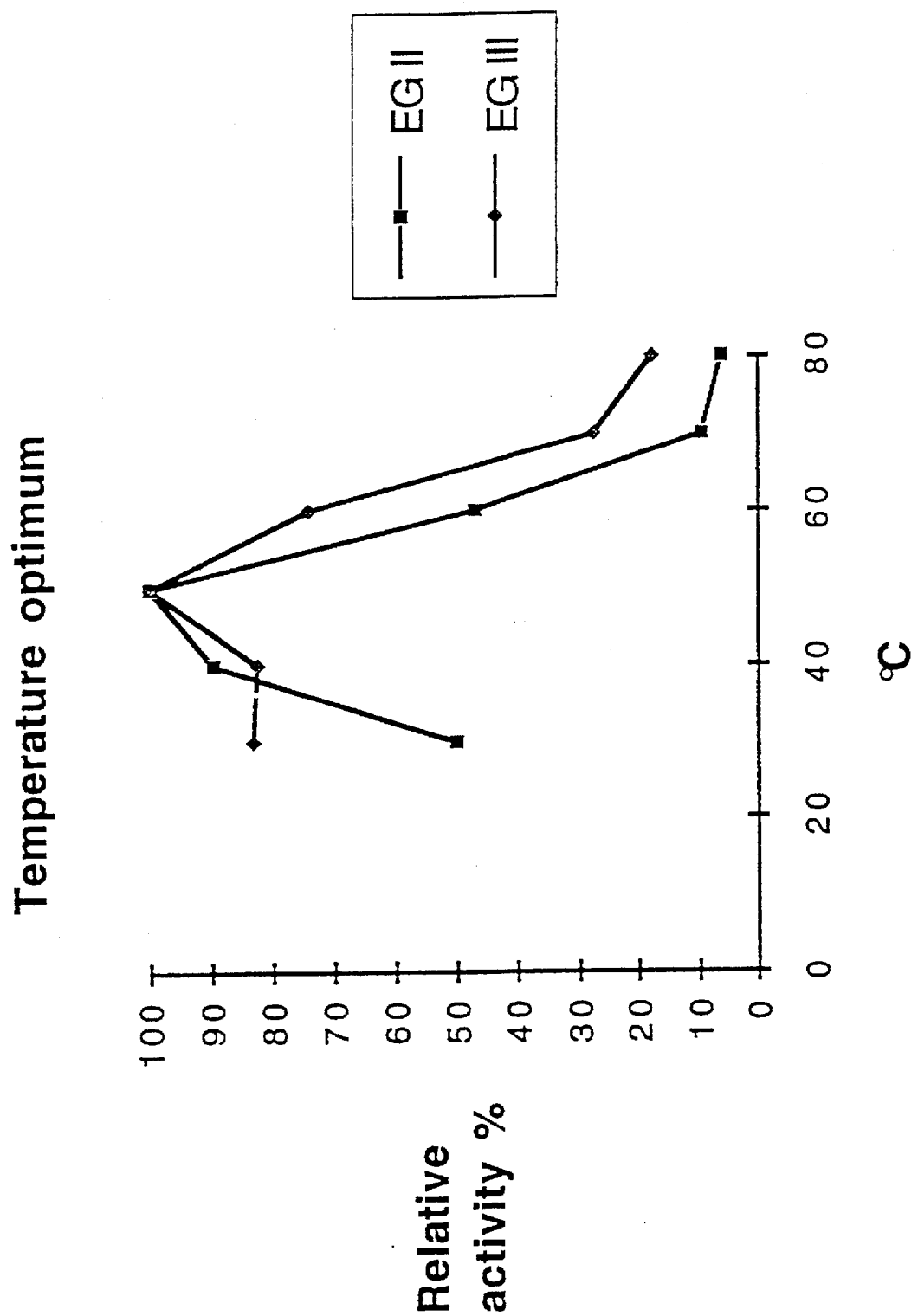
Figure 6:
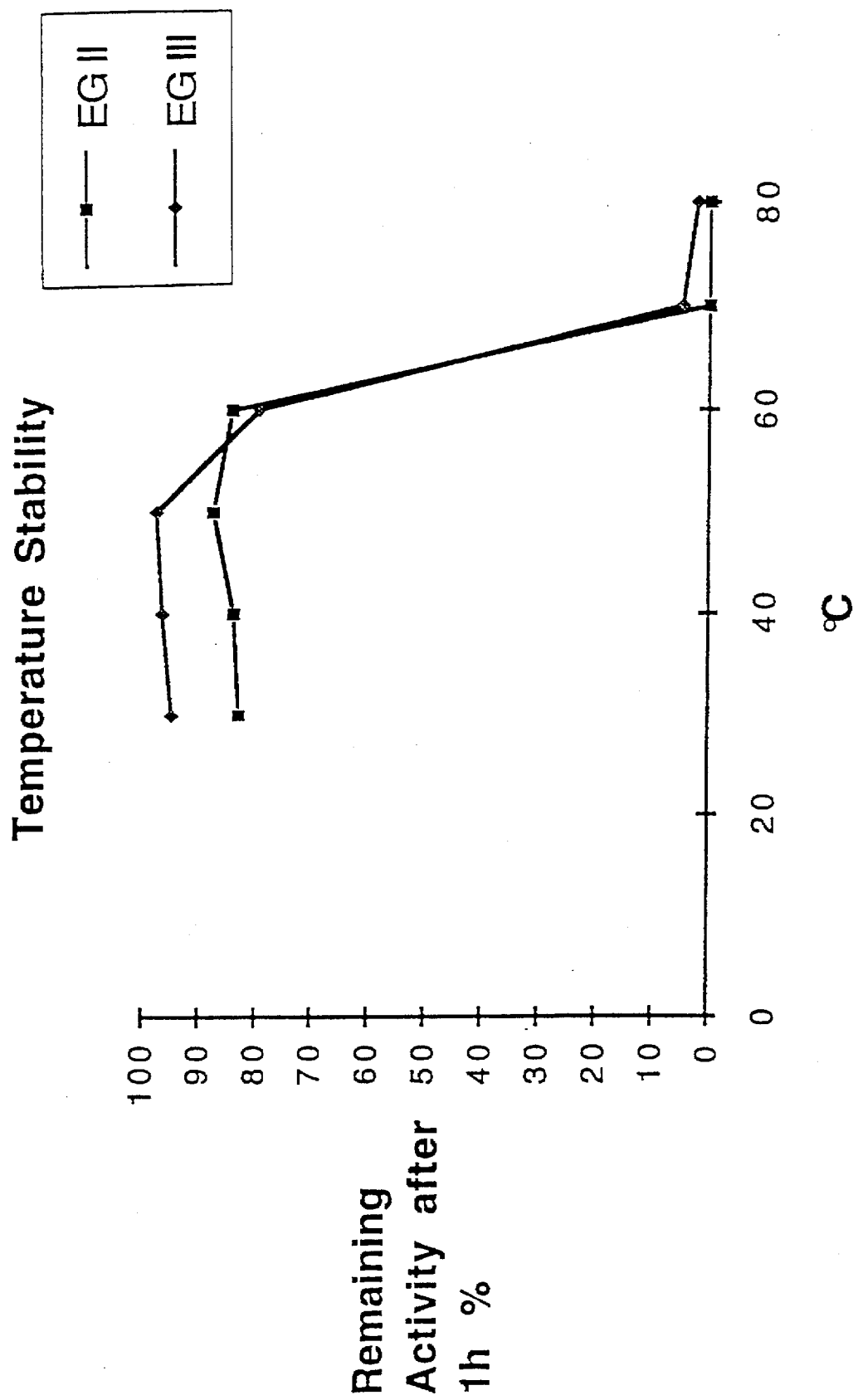

The pH optimums of the different enzymes can be seen in FIG. 3. The EG II has a pH optimum of about 3.0, EG IV of about 3.5. With respect to the pH optimum EG II and EG IV are both acidic endoglucanases showing optimal activity from pH 2.5 to 4.0 whereas EG III is optimal from pH 4.0 to 6.0.

Substrate specificity

The relative activity determined as the release of reducing sugar of the different enzymes from different polysaccharides compared to the optimal substrate (100%) is seen in the table below.

| Enzyme | EG II | EG III | EG IV |
| --- | --- | --- | --- |
| Avicell | 1% | 0% | 3% |
| CMC | 1% | 2% | 11% |
| β-glucan | 0% | 100% | 100% |
| xyloglucan | 100% | 31% | 0% |

From these results the specificities of the different endoglucanases can be calculated:

| Enzyme | EG II | EG III | EG IV |
| --- | --- | --- | --- |
| XGU/BGU | ∞ | 0.31 | 0 |
| XGU/CMC | 104 | 18 | 0 |
| XGU/AVIU | 114 | ∞ | 0 |
| BGU/XGU | 0 | 3.2 | ∞ |
| BGU/CMC | 0 | 58 | 9.4 |
| BGU/AVIU | 0 | ∞ | 25 |

The results of substrate specificity determined on AZCL-substrates is seen in the following table

| Enzyme | EG II | EG III | EG IV |
| --- | --- | --- | --- |
| HE-cellulose | 1% | 100% | 100% |
| β-glucan | 0% | 36% | 56% |
| Xyloglucan | 100% | 33% | 1% |
| Curdlan | 0% | 2% | 4% |

From the specificity results it is seen that compared to EG III and EG IV EG II is extremely specific for xyloglucan. EG III is active towards all types of substrates whereas EG IV can not degrade xyloglucan and is very specific for β-glucans. (There are some differences in the results obtained with reducing sugars and AZCL-substrates. An explanation for this is that some AZCL-substrates are more sensitive than others. In this case AZCL-HE-cellulose seems to be more sensitive than AZCL-β-glucan).

The Km and specific activity for EG II and EG III were determined as described in the Materials and Methods section above. The standard deviations on 1/Vmax and Km/Vmax obtained from the linear regression analysis were used to calculate the intervals for the enzymes apparent from the following table:

| Enzyme | Substrate | Km % substrate | Spec. act units/mg | r^2 |
|---|---|---|---|---|
| EG II | xyloglucan | 0.242–0.306 | 106–119 | 0.98 |
| EG III | β-glucan | 0.136–0.207 | 165–186 | 0.98 |

Temperature optimum and temperature/pH stability

EG II and EG III have similar temperature optimums (optimal activity between 30° C. and 60° C.) and temperature stability (stable for 1 h up to 60° C.) but EG III is more stable at high pH than EG II.

The gel filtration chromatograms, which verify the substrate specificities, show that EG II degrades xyloglucan completely into oligomers of approximately 7–9 residues which are the known repeating subunits of xyloglucans (Fry, 1989). EG III degrades xyloglucan to a much lesser extent and EG IV does not degrade xyloglucan at all. EG III degrades β-glucan to a large extent into DP 3–4 and higher oligomers. This is in accordance with β-glucans being composed of 3–4 β-1,4-linked glucose units in a row interrupted by single β-1,3-linkages. These results show that irrespective of partial homology in the DNA sequence there are remarkable differences between the three endoglucanases in substrate specificity as well as in pH optimum and stability.

REFERENCES

Aviv, H. & Leder, P. 1972. Proc. Natl. Acad. Sci. U.S.A. 69: 1408–1412.

Becker, D. M. & Guarante, L. 1991. Methods Enzymol. 194: 182–187.

Chirgwin, J. M., Przybyla, A. E., MacDonald, R. J. & Rutter, W. J. 1979. Biochemistry 18: 5294–5299.

Gubler, U. & Hoffman, B. J. 1983. Gene 25: 263–269.

Sambrook, J., Fritsch, E. F. & Maniatis, T. 1989. Molecular Cloning: A Laboratory Manual. Cold Spring Harbor Lab., Cold Spring Harbor, N.Y.

Sanger, F., Nicklen, S. & Coulson, A. R. 1977. Proc. Natl. Acad. Sci. U.S.A. 74: 5463–5467.

McDougall, G. J, and Fry, S. C, J. Plant Physiol., 1991, Vol. 137: 332–336.

Beldman, M. F. G. et al., Eur. J. Biochem., 1985, Vol. 146: 301–308.

Hayashi, T. et al., Plant Physiol., 1984, Vol. 75: 605–610.

Nishitani, K. and Tominaga, R, The Journal of Biol. Chemistry, 1992, Vol. 267, No. 29: 21058–21064.

Fry, S. et al., Biochem. J., 1992, Vol. 282: 821–828.

Fry, S., Journal of Experimental Botany, 1989, Vol. 40, No. 210: 1–11.

Christgau, S., et al., 1991, "Pancreatic β-cells express two autoantigenic forms of glutamic acid decarboxylase, a 65 kDa hydrophilic form and a 64 kDa amphiphilic form which can be both membrane-bound and soluble.". J. Biol. Chem., 266, p. 21157–212664.

Laemmli, U.K., 1970, "Cleavage of structural proteins during the assembly of the head of bacteriophage T4"., Nature, 227, p 680–685.

Sharma, S. et al., 1991, "Physical characterization of isozymes of endo-β-1,4-glucanase and β-1,4-glucosidase from Aspergillus species", FEMS Microbiology Letters 79:99–104.

Ooi, T. et al., 1990, "Complete nucleotide sequence of a gene coding for *Aspergillus aculeatus* cellulase (FI-CMCase)", Nucleic Acids Research, Vol. 18, No. 19: 5884.

Gilkes, N. R. et al., "Domains in Microbial β-1,4-Glycanases: Sequence Conservation, Function, and Enzyme Families", Microbiological Reviews, 1991, Vol. 55, No. 2: 303–315.

We claim:

1. An isolated DNA sequence comprising a member selected from the group consisting of:
   (a) the sequence of SEQ ID NO:17; and
   (b) the sequence of SEQ ID NO:18.

2. A recombinant expression vector comprising the DNA sequence of claim 1.

3. A cell comprising the recombinant expression vector of claim 2.

4. The cell of claim 3, wherein the cell is a eukaryotic cell.

5. The cell of claim 4, wherein the eukaryotic cell is a fungal cell.

6. The cell of claim 5, wherein the fungal cell is a yeast or a filamentous fungal cell.

7. The cell of claim 6, wherein the cell belongs to a strain of Aspergillus.

8. The cell of claim 7, wherein the Aspergillus strain is *Aspergillus niger* or *Aspergillus oryzae*.

9. A method of producing an enzyme exhibiting endoglucanase activity, the method comprising culturing the cell of claim 3 under conditions permitting the production of the enzyme, and recovering the enzyme from the culture.

10. An isolated DNA sequence comprising the sequence of SEQ ID NO:19.

11. A recombinant expression vector comprising the DNA sequence of claim 10.

12. A cell comprising the recombinant expression vector of claim 11.

13. The cell of claim 12, wherein the cell is a eukaryotic cell.

14. The cell of claim 13, wherein the eukaryotic cell is a fungal cell.

15. The cell of claim 14, wherein the fungal cell is a yeast or a filamentous fungal cell.

16. The cell of claim 15, wherein the cell belongs to a strain of Aspergillus.

17. The cell of claim 16, wherein the Aspergillus strain is *Aspergillus niger* or *Aspergillus oryzae*.

18. A method of producing an enzyme exhibiting endoglucanase activity, the method comprising culturing the cell of claim 12 under conditions permitting the production of the enzyme, and recovering the enzyme from the culture.

* * * * *

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( x i ) SEQUENCE DESCRIPTION: SEQ ID NO:1:

ATTCATTTGT GGACAGTGGA C  21

( 2 ) INFORMATION FOR SEQ ID NO: 2:

( i ) SEQUENCE CHARACTERISTICS:

(A) LENGTH: 20 base pairs
(B) TYPE: nucleic acid
(C) STRANDEDNESS: single
(D) TOPOLOGY: linear (xi) SEQUENCE DESCRIPTION: SEQ ID NO: 2:

GTTGATCGCA CATTGAACCA                    20

(2) INFORMATION FOR SEQ ID NO: 3:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO: 3:

ACCCCAGCCG ACCGATTGTC                    20

(2) INFORMATION FOR SEQ ID NO: 4:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO: 4:

CTTCCTTACC TCACCATCAT                    20

(2) INFORMATION FOR SEQ ID NO: 5:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO: 5:

TTAACATCTT TTCACCATGA                    20

(2) INFORMATION FOR SEQ ID NO: 6:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO: 6:

AGCTTTCCCT TCTCTCCCTT                    20

(2) INFORMATION FOR SEQ ID NO: 7:

(i) SEQUENCE CHARACTERISTICS:
(A) LENGTH: 28 base pairs
(B) TYPE: nucleic acid
(C) STRANDEDNESS: single
(D) TOPOLOGY: linear (xi) SEQUENCE DESCRIPTION: SEQ ID NO: 7:

GCCACCCTGG CTTCCGCTGC CAGCCTCC           28

(2) INFORMATION FOR SEQ ID NO: 8:

(i) SEQUENCE CHARACTERISTICS:
(A) LENGTH: 20 base pairs
(B) TYPE: nucleic acid ( C ) STRANDEDNESS: single
        ( D ) TOPOLOGY: linear ( x i ) SEQUENCE DESCRIPTION: SEQ ID NO: 8:

GACAGTAGCA ATCCAGCATT                                                                    20

( 2 ) INFORMATION FOR SEQ ID NO: 9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 9:

AGCATCAGCC GCTTTGTACA                                                                    20

( 2 ) INFORMATION FOR SEQ ID NO: 10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 10:

CCATGAAGTT CACCGTATTG                                                                    20

( 2 ) INFORMATION FOR SEQ ID NO: 11:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 11:

GCACTGCTTC TCTCCCAGGT                                                                    20

( 2 ) INFORMATION FOR SEQ ID NO: 12:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 12:

GTGGGCGGCC CCTCAGGCAA                                                                    20

( 2 ) INFORMATION FOR SEQ ID NO: 13:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 13:

ACGCTCCTCC AATTTCTCT                                                                     20

( 2 ) INFORMATION FOR SEQ ID NO: 14:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 14:

GGCTTGGTAG TAATGAGTCT                                                                                    20

( 2 ) INFORMATION FOR SEQ ID NO: 15:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 15:

GGCGCAGAGT TTGGCCAGGC                                                                                    20

( 2 ) INFORMATION FOR SEQ ID NO: 16:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 16:

CAACATCCCC GGTGTTCTGG G                                                                                  21

( 2 ) INFORMATION FOR SEQ ID NO: 17:

( i ) SEQUENCE CHARACTERISTICS:
        ( A ) LENGTH: 347 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 17:

| AAAGATTCAT | TTGTGGACAG | TGGACGTTGA | TCGCACATTG | AACCAACCCC | AGCCGACCGA | 60 |
|---|---|---|---|---|---|---|
| TTGTCCTTCC | TTACCTCACC | ATCATTTAAC | ATCTTTTCAC | CATGAAGCTT | TCCCTTCTCT | 120 |
| CCCTTGCCAC | CCTGGCTTCC | GCTGCCAGCC | TCCAGCGCCG | CACACTTCTG | CGGTCAGTGG | 180 |
| GATACCGCCA | CCGCCGGTGA | CTTCACCCTG | TACAACGACC | TTTGGGGCGA | GACGGCCGGC | 240 |
| ACCGGCTCCC | AGTGCACTGG | AGTCGACTCC | TACAGCGGCG | ACACCATCGC | TTGTCACACC | 300 |
| AGCAGGTCCT | GGTCGGAGTA | GCAGCAGCGT | CAAGAGCTAT | GCCAACG | | 347 |

( 2 ) INFORMATION FOR SEQ ID NO: 18:

( i ) SEQUENCE CHARACTERISTICS:
        ( A ) LENGTH: 294 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 18:

| CAGCATCTCC | ATTGAGTAAT | CACGTTGGTG | TTCGGTGGCC | CGCCGTGTTG | CGTGGCGGAG | 60 |
|---|---|---|---|---|---|---|
| GCTGCCGGGA | GACGGGTGGG | GATGGTGGTG | GGAGAGAATG | TAGGGCGCCG | TGTTTCAGTC | 120 |
| CCTAGGCAGG | ATACCGGAAA | ACCGTGTGGT | AGGAGGTTTA | TAGGTTTCCA | GGAGACGCTG | 180 |
| TATAGGGGAT | AAATGAGATT | GAATGGTGGC | CACACTCAAA | CCAACCAGGT | CCTGTACATA | 240 |
| CAATGCATAT | ACCAATTATA | CCTACCAAAA | AAAAAAAAA | AAAAAAAAA | AAAA | 294 |

( 2 ) INFORMATION FOR SEQ ID NO: 19:

( i ) SEQUENCE CHARACTERISTICS:
        ( A ) LENGTH: 181 base pairs ( B ) TYPE: nucleic acid
( C ) STRANDEDNESS: single
( D ) TOPOLOGY: linear ( x i ) SEQUENCE DESCRIPTION: SEQ ID NO: 19:

```
GACAGTAGCA  ATCCAGCATT  AGCATCAGCC  GCTTTGTACA  CCATGAAGTT  CACCGTATTG      60

GCACTGCTTC  TCTCCCAGGT  GTGGGCGGCC  CCTCAGGCAA  ACGCTCCTCC  AATTTTCTCT     120

GGCTTGGTAG  TAATGAGTCT  GGCGCAGAGT  TTGGCCAGGC  CAACATCCCC  GGTGTTCTGGG    181
```